United States Patent [19]

Dryden

[11] 3,960,148

[45] June 1, 1976

[54] APPARATUS FOR HIGH FLOW ANESTHESIA

[76] Inventor: Gale E. Dryden, 5835 N. Tacoma Ave., Indianapolis, Ind. 46220

[22] Filed: Oct. 15, 1974

[21] Appl. No.: 514,390

[52] U.S. Cl. .............................. 128/188; 128/145.7; 128/202
[51] Int. Cl.² ....................................... A61M 16/00
[58] Field of Search .......... 128/188, 202, 203, 194, 128/195, 205, 145 R, 145.5, 145.6, 145.7, 145.8, 146, 146.3, 146.4, 142, 142.4, 147, 174

[56] References Cited
UNITED STATES PATENTS

| 3,467,094 | 9/1969 | Goodman | 128/142 |
|---|---|---|---|
| 3,730,179 | 5/1973 | Williams | 128/145.5 |

FOREIGN PATENTS OR APPLICATIONS

| 1,323,401 | 2/1963 | France | 128/205 |

Primary Examiner—Robert W. Michell
Assistant Examiner—Henry J. Recla
Attorney, Agent, or Firm—Woodard, Weikart, Emhardt & Naughton

[57] ABSTRACT

A safe anesthetic mixture is supplied through a humidifier unit and passageway to a mask. The humidifier unit and passageway are incorporated in a device having an inlet nipple for connection to the delivery hose from a gas machine, a nipple for connection directly to a mask, and a nipple for connection directly to a rebreathing bag, with a common chamber therebetween, and a valved passageway and outlet nipple for connection to an exhaust line. The great majority of the exhaled mixture is removed through the rebreathing bag and exhaust line. Since very little of the anesthetic mixture is rebreathed, this device avoids the necessity for a carbon dioxide absorber.

12 Claims, 2 Drawing Figures

U.S. Patent  June 1, 1976  3,960,148
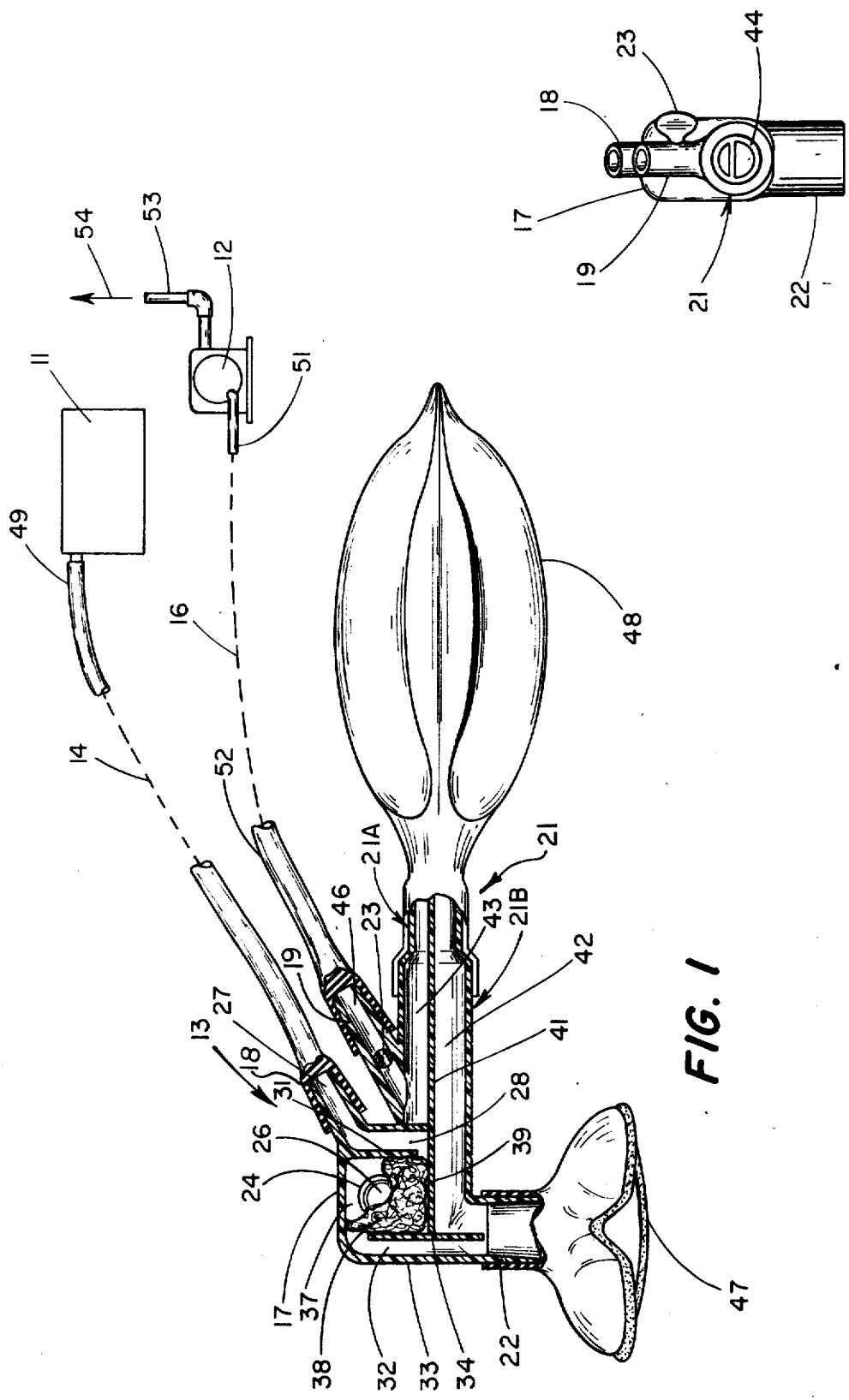

3,960,148

APPARATUS FOR HIGH FLOW ANESTHESIA

BACKGROUND OF THE INVENTION

1. Field of the Invention

This invention relates generally to anesthesia, and more particularly to convenient means for avoiding the necessity of absorption of carbon dioxide during the application of an anesthetic mixture.

2. Description of the Prior Art

Heretofore, in order to conserve anesthetic gases, and thereby achieve significant economies, typical practice, particularly for protracted periods of anesthesia, has been to employ a circle absorber system, in which air exhaled by the patient is passed through a carbon dioxide absorber, and rebreathed. It is known that by providing a sufficiently high volume of fresh anesthetic mixture to a patient, and by providing means for the exhaled gases to be dispensed to the atmosphere without re-inhalation of excessive carbon dioxide, anesthesia can be performed without the use of a carbon dioxide absorber, and still avoid carbon dioxide poisoning of the patient. However, such procedures have been considered by many to be wasteful of anesthetic gases and therefore extravagant and expensive. Also they have involved a fairly clumsy assortment of components and fittings. In addition, the exhaled mixture presents problems in the operating room environment, if not necessarily from tendency to stablish a fire supporting environment, at least from the standpoint of biologically contaminating the environment in some cases, and tending to contribute to an anesthetic environment in the operating room itself. Nevertheless, I believe there are situations where the problems of such procedures can be minimized, and some advantages achieved. My present invention is directed toward securing the advantages and minimizing the problems.

SUMMARY OF THE INVENTION

In a typical embodiment of this invention, the apparatus comprises a compact housing having therein a humidifier unit, said humidifier unit having an inlet passageway and an outlet passageway, and said humidifier unit having means for continuously receiving a fresh anesthetic mixture through said inlet passageway. The housing has means for connection of a mask and rebreathing bag thereto. It also has means for connection to an exhaust exit line whereby contents of the rebreathing bag may be removed from the assembly, and there is very little rebreathing of anesthetic mixture.

It is an object of this invention to provide a high flow anesthetic assembly which does not require means for carbon dioxide absorption.

It is a further object of this invention to provide a high flow anesthetic assembly which does not contaminate the operating room atmosphere with exhaled gases.

It is a still further object of this invention to provide a high flow anesthetic assembly which is completely disposable.

These and related objects will become apparent from the following description of the preferred embodiment.

BRIEF DESCRIPTION OF THE DRAWINGS

FIG. 1 is a schematic drawing of a typical embodiment of the high flow anesthetic assembly of this invention, showing the housing in longitudinal section and on a much larger scale than the gas machine and vacuum source, and showing the rebreathing bag and mask.

FIG. 2 is an end view of the housing itself.

DESCRIPTION OF THE PREFERRED EMBODIMENT

Referring now to the drawings in detail, a highflow anesthesia system is shown in FIG. 1 partially schematically with a conventional gas machine 11 and a vacuum pump 12, both shown on a very small scale, and connected to the junction unit 13 of the present invention, which is shown on a much larger scale, there being dotted lines at 14 and 16 accommodating the transition between the two scales on the drawing. The unit 13 includes a housing 17 typically molded of plastic in two halves joined at the cutting plane for the illustration of FIG. 1. The housing includes an inlet nipple 18 for a fresh anesthetic mixture from the gas machine 11, and an outlet 19 for connection to the vacuum pump 12. It includes a stepped nipple 21 connected to a rebreathing bag, and a nipple 22 connected to a mask. A valve 23 is located in the nipple 19 and can be used to shut off flow therethrough. A hole 24 is provided in the wall of the housing and receives a rubber or plastic plug 26.

In addition to the inlet passageway 27 in the nipple 18, there is an entrance passageway 28 provided between the wall 29 and a partition 31. Similarly, there is a passageway 32 provided by wall 33 and partitions 34 and 36. Between the partitions 31 and 34, is a chamber 37 with which the wall opening 24 is in communication. In this chamber there is a humidifier pad 38 of an absorbent material. A material such as used in surgical sponges, or "Band-Aid" bandages or mechanics' waste, may be used and saturated with water. Although it fills chamber 37, it is shown only fragmentarily, in order to enable showing the inner end of plug 26 in the drawing.

An interior wall 39–41 extends throughout the length of the unit and provides a shuttle chamber 42 communicating between the nipple 22 and nipple 21. Also it provides an exit passageway 43 between the end 44 of the nipple 21, and the outlet passageway 46 in the outlet nipple 19.

The housing can be made of inexpensive plastic material; is about hand-sized, or smaller, being typically about four and onehalf inches long, two inches high, and one inch wide.

Typically the nipples are sized and shaped to accommodate conventional sizes of hoses used in anethesia. For example, the inside diameter of the nipple 22 is nominally 15 millimeters, while the outside diameter is 22 millimeters. The outside diameter of the smaller step on the nipple 21 is 15 millimeters at 21A and 22 millimeters at 21B. The outside diameters on the nipples 18 and 19 is approximately 3/10 of an inch with about a 4 degree taper. Thus, the housing is small, light in weight, convenient to use, and disposable.

In the use of the apparatus according to a typical embodiment of the present invention, a mask 47, which can be conventional in nature, is connected directly to the fitting 22. A rebreathing bag 48, also of conventional construction, is connected directly to the nipple 21. The gas deliery hose 49 of the gas machine is connected directly to the nipple 18, and a vacuum line 51 is connected by a hose 52 to the nipple 19. The vacuum line 51 may be a part of the equipment of a building, but it is desirable that the discharge from the vacuum pump 12 on line 53 be directed outside the building to atmosphere as indicated schematically at 54. Thereby, any anesthetics, or combustion supporting mixtures, or biologically contaminated mixtures, will not be discharged inside the building.

Prior to use of the apparatus, the humidifier pad may be replaced or renewed by removal of the plug 26 from the opening 24, withdrawal of the old pad therethrough, and insertion of the new pad. It should be packed sufficiently to avoid channeling, and thus assure full contact of the moisture therein by the anesthetic mixture incoming through entrance passageway 28. Yet it should permit adequate flow of ten to fifteen liters per minute at a pressure of about fifteen pounds per square inch on the inlet side of nipple 18.

The humidifier pad may be moistened by simply pouring eight to ten cc. of water into the nipple 18. If it is desired to moisten the pad during actual anesthesia, a hypodermic needle can be passed through the plug 26 which may be made of rubber and thereby penetrable by a conventional hypodermic needle, with the water being injected thereby into the pad from a hypodermic syringe, the thickness and resilience of the rubber being sufficient to reseal the puncture after removal of the needle. Other materials might also be used.

Typically, the face mask is shaped for completely covering the nose and mouth of the patient, thereby preventing atmospheric contamination of the anesthetic mixture, and vice-versa. The rebreathing bag is provided to allow the patient to breathe normally. As the patient inhales, he receives fresh anesthetic mixture which enters through the nipple 18, is humidified in chamber 37 by the moist humidifier pad 38, and passes through the passageway 32 and mask into his lungs. The mixture will be supplied at a rate approximately two and one-half times the normal breathing volume for the patient. This will usually be a rate of approximately 10 to 15 liters per minute supplied by the machine 11, and it is established conventionally by flowmeter settings on the gas machine 11. The nature of the mixture will depend upon the preferences and determinations of the anesthesiologist, considering the requirements of the patient. One example might be a combination of nitrous oxide, with oxygen, and a volatile agent such as halothane or, penthane, for example.

As the patient exhales, the rebreathing bag is inflated, and not only the exhaled mixture, but also a part of the continously incoming fresh mixture, is introduced into the chamber 42. When the patient again inhales, he inhales primarily fresh mixture through the pssageway 32, and possibly a slight amount of combination of fresh and exhaled mixture from the shuttle chamber 42. Meanwhile, the vacuum connected to the exit passageway 43 withdraws the remaining exhaled mixture in an amount approximately equal to that of fresh mixture supplied by the gas machine. The finger operable valve 23 is useful to control the amount of vacuum on the passageway 46.

For several years, I have developed apparatus of an expendable disposable nature, which is useful in anesthesia but can be discarded after use, thus materially decreasing the likelihood of cross-contamination between patients, which sometimes occurs where some of the same components are used on several patients. One disposable component is a carbon dioxide absorber. Now that plastic materials used in such absorbers have become comparatively scarce, the present invention provides a very satisfactory solution to the problem, because the housing requires a very small amount of plastic for its construction, being hand-sized. Also, if necessary, it can be "auto-claved", with or without the absorbent pad therein, and reused. Of course the hoses, mask, and rebreathing bag can be auto-claved also, or they can be of disposable material if desired.

The invention claimed is:

1. A high flow anesthetic administration unit comprising:
   a housing having therein first, second, third, and fourth connection means for connection thereto of gas handling devices, said first means being an inlet for reception of fresh anesthetic mixture, said second means being an outlet-inlet for direct connection to a breathing mask, said third means being an outlet for direct connection to a rebreathing bag, and said fouth means being an outlet for connection to a vacuum line, and said housing having partition means therein defining portions of a single gas flow path in said housing from said first connection means to said second connection means and from said second connection means to said third connection means;
   a humidifier in the portion of said flow path from said first to said second connection means, to humidify fresh mixture during passage from said first connection means through said housing to said second connection means, said partition means further dividing said third connection means into first and second flow paths thereby providing a single gas flow path from said second connection means to said first flow path of said third connection means and another single gas flow path from said second flow path of said third connection means to said fourth connection means whereby, when a rebreathing bag is connected to said third connection means, a single gas flow path is established from said second connection means to said fourth connection means via the rebreathing bag.

2. The apparatus of claim 1 wherein:
   the material of said housing is of an expendable plastic.

3. The apparatus of claim 1 wherein:
   the maximum dimension of said housing in any direction is less than 5 inches.

4. The apparatus of claim 1 wherein:
   said humidifier is a wet pad extending completely across the path portion communicating between said first and second connection means whereby all gas passing through said path portion must pass through said pad and will be thereby humidified.

5. A high flow anesthetic administration unit comprising:
   a housing having therein first, second, third, and fourth connection means for connection thereto of gas handling devices, said first means being an inlet for reception of fresh anesthetic mixture, said second means being an outlet-inlet for direct connection to a breathing mask, said third means being an outlet for direct connection to a rebreathing bag, and said fourth means being an outlet for connection to a vacuum line;
   a humidifier in an only path in said housing between said first and second connection means, to humidify fresh mixture during passage from said first means through said housing to said second means, and partition means dividing said third connection means into first and second flow paths and defining a single gas flow path from said first connection means to said second connection means and from said second connection means to said first flow path of said third connection means and another single gas flow path from said second flow path of said third connection means to said fourth connection means, whereby when a rebreathing bag is connected to said third connection means, a single gas flow path is established from said second connection means to said fourth connection means;

said housing having a wall portion at said humidifier, said portion being penetrable by a hypodermic needle to facilitate addition of water to the humidifier, said wall portion being self-sealing upon removal of the needle.

6. The apparatus of claim 5 wherein:

said wall portion is a rubber plug.

7. A high flow anesthetic administration unit comprising:

a housing having therein first, second, third, and fourth connection means for connection thereto of gas handling devices, said first means being an inlet for reception of fresh anesthetic mixture, said second means being an outlet-inlet for direct connection to a breathing mask, said third means being an outlet for direct connection to a rebreathing bag, and said fourth means being an outlet for connection to a vacuum line;

a humidifier in an only path in said housing between said first and second connection means, to humidify fresh mixture during passage from said first means through said housing to said second means, and partition means dividing said third connection means into first and second flow paths and defining a single gas flow path from said first connection means to said second connection means and from said second connection means to said first flow path of said third connection means and another single gas flow path from said second flow path of said third connection means to said fourth connection means, whereby when a rebreathing bag is connected to said third connection means, a single gas flow path is established from said second connection means to said fourth connection means;

a manually operable valve in a path between said third and fourth connection means.

8. A high flow anesthetic administration unit comprising:

a housing having therein first, second, third, and fourth connection means for connection thereto of gas handling devices, said first means being an inlet for reception of fresh anesthetic mixture, said second means being on outlet-inlet for direct connection to a breathing mask, said third means being an outlet for direct connection to a rebreathing bag, and said fourth means being an outlet for connection to a vacuum line;

a humidifier in an only path in said housing between said first and second connection means, to humidify fresh mixture during passage from said first means through said housing to said second means, and partition means dividing said third connection means into first and second flow paths and defining a single gas flow path from said first connection means to said second connection means and from said second connection means to said first flow path of said third connection means and another single gas flow path from said second flow path of said third connection means to said fourth connection means, whereby when a rebreathing bag is connected to said third connection means, a single gas flow path is established from said second connection means to said fourth connection means; and a gas machine having gas delivery conduit means connected to said first connection means, a mask connected to said second connection means, a rebreathing bag connected to said third connection means, and a vacuum source connected to said fourth connection means.

9. The apparatus of claim 8 wherein:

said gas machine is a machine supplying an anesthetic mixture at a rate of from about ten liters per minute to about fifteen liters per minute.

10. The apparatus of claim 9 wherein:

said humidifier includes a porous pad, saturated with water, and in communication with all of the anesthetic mixture entering said housing, prior to discharge from said housing.

11. The apparatus of claim 10 and further comprising:

a hand-operated valve in an only passageway in said housing between said third and fourth connection means.

12. The apparatus of claim 11 wherein the anesthetic mixture comprises the combination of:

nitrous oxide, oxygen, and a volatile agent.

* * * * *